United States Patent
Park et al.

(10) Patent No.: US 11,040,007 B2
(45) Date of Patent: Jun. 22, 2021

(54) INJECTION COMPOSITION CONTAINING ACETAMINOPHEN

(71) Applicant: WOOSUNG PHARMACEUTICAL CO., LTD., Gyeonggi-do (KR)

(72) Inventors: Jong Woo Park, Gyeonggi-do (KR); Jeong Rae Cho, Gyeonggi-do (KR)

(73) Assignee: WOOSUNG PHARMACEUTICAL CO., LTD., Gyeonggi-do (KR)

( * ) Notice: Subject to any disclaimer, the term of this patent is extended or adjusted under 35 U.S.C. 154(b) by 0 days.

(21) Appl. No.: 16/480,015

(22) PCT Filed: Jan. 24, 2018

(86) PCT No.: PCT/KR2018/001039
§ 371 (c)(1),
(2) Date: Jul. 23, 2019

(87) PCT Pub. No.: WO2018/139842
PCT Pub. Date: Aug. 2, 2018

(65) Prior Publication Data
US 2019/0380950 A1    Dec. 19, 2019

(30) Foreign Application Priority Data
Jan. 24, 2017  (KR) .................. 10-2017-0011251

(51) Int. Cl.
| | | |
|---|---|---|
| *A61K 9/00* | (2006.01) | |
| *A61K 31/167* | (2006.01) | |
| *A61K 47/18* | (2017.01) | |
| *A61K 47/20* | (2006.01) | |
| *A61K 47/26* | (2006.01) | |

(52) U.S. Cl.
CPC .......... *A61K 9/0019* (2013.01); *A61K 31/167* (2013.01); *A61K 47/183* (2013.01); *A61K 47/20* (2013.01); *A61K 47/26* (2013.01)

(58) Field of Classification Search
None
See application file for complete search history.

(56) References Cited

U.S. PATENT DOCUMENTS

| | | | |
|---|---|---|---|
| 6,288,067 B1 | 9/2001 | Okamura et al. | |
| 9,089,477 B2 * | 7/2015 | Al Dandachi Atassi | ................... A61K 31/166 |
| 9,399,012 B2 * | 7/2016 | Royal | .............. A61K 47/22 |
| 2002/0142991 A1 * | 10/2002 | Herzenberg | ............ A61P 31/04 514/49 |
| 2011/0117194 A1 | 5/2011 | Kim et al. | |

FOREIGN PATENT DOCUMENTS

| | | | | |
|---|---|---|---|---|
| EP | 2649993 A1 * | 10/2013 | ............. | A61P 25/04 |
| JP | 2015-214576 | 12/2015 | | |
| KR | 10-2013-0132496 | 12/2013 | | |

OTHER PUBLICATIONS

Dribben et a. (Stability and Microbiology of Inhalant N-Acetylcysteine Used as an Intravenous Solution for the treatment of Acetaminophen Poisoning, Annals of Emergency Medicine, Jul. 2003, 42:1. (Year: 2003).*
Dribben et al. (Stability and Microbiology of Inhalant N-Acetylcysteine Used as an Intravenous Solution for the treatment of Acetaminophen Poisoning, Annals of Emergency Medicine, Jul. 2003, 42:1). (Year: 2003).*
Garekani et al. (Increasing the aqueous solubility of acetaminophen in the presence of polyvinylpyrrolidone and investigation of the mechanisms involved, Drug Development and Industrial Pharmacy, 2003, vol. 29. No. 2 pp. 173-179. (Year: 2003).*
International Search Report dated Apr. 26, 2018 for PCT/KR2018/001039.
Dribben, W. H. et al., "Stability and microbiology of inhalant N-acetylcysteine used as an intravenous solution for the treatment of acetaminophen poisoning", Annals of Emergency Medicine, 2003, vol. 42, pp. 9-13.
Garekani, H. A. et al., "Increasing the aqueous solubility of acetaminophen in the presence of polyvinylpyrrolidone and investigation of the mechanisms involved", Drug Development and Industrial Pharmacy, 2003, vol. 29, No. 2, pp. 173-179.

* cited by examiner

*Primary Examiner* — Melissa S Mercier

(57) ABSTRACT

The present disclosure relates to the injection composition containing acetaminophen, the injection composition comprising acetaminophen mixed in 0.01~5 wt %, a solubilizer mixed in 0.01~10 wt %, a toxicity inhibitor mixed in 0.05~5 wt %, an isotonic agent mixed in 0.1~10 wt %, an antioxidant mixed in 0.001~5 wt %, and the balance sterile purified water for injection.

6 Claims, No Drawings

INJECTION COMPOSITION CONTAINING ACETAMINOPHEN

TECHNICAL FIELD

The present invention relates to an injection composition containing acetaminophen.

BACKGROUND ART

Acetaminophen is a para-aminophenol-based drug and is the most widely used antipyretic analgesic on the market. Acetaminophen is a non-narcotic antipyretic analgesic that acts to the central nervous system, and has relatively short recovery time after treatment because it does not have drug dependency which is a characteristic of narcotic analgesics acting to the central nervous system, and medical expense that a patient has to bear is inexpensive. In addition, since acetaminophen acts to the central nervous system, it achieves drug effect faster than nonsteroidal anti-inflammatory analgesics (NSAID) acting to peripheral nervous system, and in contrast to NSAID, it does not cause side effects such as cardiovascular side effect or bleeding, platelet aggregation inhibition, gastrointestinal side effects, induction of asthma, renal disorder, or the like.

Acetaminophen is usually administered orally in the form of tablets, syrups and the like. Since acetaminophen has low solubility in an aqueous solution, when it is prepared in the form of an injection, recrystallization may be precipitated in a distribution process, and thus it cannot be used and may be disposed. In addition, when injected into a human body in the state in which recrystallization is precipitated, the injection containing acetaminophen may cause vascular embolism, which may have a deadly influence on a patient's life. Acetaminophen is unstable in an aqueous solution, and in particular, the stability of acetaminophen is influenced by a pH. It has been known that acetaminophen may be hydrolyzed in an acidic or basic environment, and hydrolysis occurs at a minimum as the pH approaches 6. In addition, acetaminophen is decomposed in the presence of oxygen and light, and can exhibit hepatotoxicity due to benzoquinone imine which is acetaminophen degradation product. Therefore, an injection containing acetaminophen should be carefully handled in the manufacturing and distribution processes.

On the other hand, the current commercially available injection containing acetaminophen has a concentration of drug of 10 mg/ml and is intended to be instilled for 15 minutes. In addition, the injection containing acetaminophen has a storage temperature of 20 to 25° C., and is prohibited to be stored in a frozen or refrigerated state. This is because there is a risk that the injection containing acetaminophen cause recrystallization of the drug when the temperature is lowered and this causes problems in terms of efficacy, safety, or the like at the time of injection.

In addition, in patients with long-term or overdose of acetaminophen, alcoholics and undernourished patients, patients with insufficient glutathione reserves such as acquired immunodeficiency patients, patients with increased CYP2E1 activity caused by simultaneously administering both anticonvulsant and anti-tuberculosis drug, due to the high likelihood of liver damage, a lot of caution is required, such as conducting a liver function test before administering the injection containing acetaminophen.

In addition, many drug addictions and suicides caused by improper use of acetaminophen have been reported every year, and hepatotoxicity due to acetaminophen is also the major cause of serious illness and death.

According to a number of clinical trial results, it has been found that hepatotoxicity induced by acetaminophen can be prevented and can be effectively treated through an early diagnosis and a real-time administration of N-acetylcysteine (NAC) that is an antidote. However, since prognosis is the best when detoxification is conducted within 8 hours after drug addiction, early detection is important in the treatment of overdose of acetaminophen. Initial symptoms of acetaminophen addiction include discomfort, nausea and vomiting. However, some patients may not show syndrome of addiction at an early stage of drug addiction, even when the concentration of acetaminophen in the blood reaches the level of addiction and liver function is abnormal.

In order to treat this addiction of acetaminophen, N-acetylcysteine is orally administered or intravenously injected. However, many problems that side effects occur due to excessive administration of N-acetylcysteine during a course of treatment have been reported.

In the case of treating a patient suffering from drug addiction caused by acetaminophen, there is an inconvenience that a patient has to detoxify through a complicated step, and accordingly, difficulties such as the increase in medical expenses are accompanied.

DISCLOSURE OF THE INVENTION

Technical Problem

The present invention relates to an injection composition containing acetaminophen, which can secure low temperature stability during distribution, efficacy and safety during use, and can reduce or prevent hepatotoxicity.

Technical Solution

An injection composition containing acetaminophen of the present invention may include, with respect to whole composition, acetaminophen mixed in the amount of 0.01 to 5 wt %, a solubilizing agent mixed in the amount of 0.01 to 10 wt %, a toxic inhibiting material mixed in the amount of 0.05 to 5 wt %, an isotonic agent mixed in the amount of 0.1 to 10 wt %, an antioxidant mixed in the amount of 0.001 to 5 wt %, and the rest of sterile purified water for injection.

In addition, the injection composition may have a pH of 4 to 8.

Also, the solubilizing agent may be a cationic amino acid, a nonpolar amino acid or a water-soluble polymer. The cationic amino acid may be any one selected from arginine, histidine and lysine, or a mixture thereof. The nonpolar amino acid may be any one selected from valine, leucine, isoleucine, proline, phenylalanine and tryptophan, or a mixture thereof. The water-soluble polymer may be any one selected from povidone (Kollidon 12PF or Kollidon 17PF), poloxamer, polyethyleneglycol and polysorbate, and a mixture thereof. The solubilizing agent may be mixed in the amount of 0.01 to 10 wt % in the whole injection composition.

In addition, the toxic inhibiting material may be any one selected from N-acetylcysteine (NAC), methionine and glutathione, or a mixture thereof. The toxic inhibiting material may be mixed in the amount of 0.05 to 5 wt % in the whole injection composition.

Furthermore, the isotonic agent may be selected from sugar alcohols, which include mannitol, erythritol, glucose or trehalose, and sodium chloride (NaCl), or a mixture thereof. The isotonic agent may be mixed in the amount of 0.1 to 10 wt % in the whole injection composition.

The antioxidant may be any one selected from sodium bisulfite, sodium pyrosulfite and cysteine, or a mixture thereof. The antioxidant may be mixed in the amount of 0.001 to 5 wt % in the whole injection composition.

Advantageous Effects

The injection composition containing acetaminophen of the present invention can prevent the occurrence of recrystallization caused by a lowering of solubility of acetaminophen when the injection composition is stored at room temperature or less, thereby secure of storage stability.

In addition, the injection composition containing acetaminophen of the present invention can prevent shocks and the like that may occur in a patient when used, and prevent or reduce the occurrence of hepatotoxicity caused by excessive administration, thereby securing efficacy and safety when using the injection.

MODE FOR CARRYING OUT THE INVENTION

Hereinafter, an injection composition containing acetaminophen according to an embodiment of the present invention is described.

An injection composition containing acetaminophen according to an embodiment of the present invention contains acetaminophen, a solubilizing agent, a toxic inhibiting material, an isotonic agent, and an antioxidant. The injection composition may contain sterile purified water, which has been used for injection, as a balance. The injection composition increases solubility of acetaminophen in an aqueous solution to increase stability at a low temperature, and prevents or reduces hepatotoxicity caused by acetaminophen.

Acetaminophen is added to the whole injection composition in an amount of 0.01 to 5 wt %. Acetaminophen may be mixed in the amount of preferably 0.1 to 5 wt %, and more preferably 0.5 to 2 wt %. When the content of acetaminophen is too small, expression of the pharmacological effect may be lowered or a dose of the injection to be injected once may be increased. In addition, when the content of acetaminophen is too high, precipitation may be occurred in the injection due to the solubility problem.

The solubilizing agent may be a cationic amino acid, a nonpolar amino acid or a water-soluble polymer. The solubilizing agent may be a mixture of two or three substances selected from the cationic amino acid, the nonpolar amino acid, and the water-soluble polymer. The cationic amino acid may be any one selected from arginine, histidine and lysine, or a mixture thereof. The nonpolar amino acid may be any one selected from valine, leucine, isoleucine, proline, phenylalanine and tryptophan, or a mixture thereof. The water-soluble polymer may be any one selected from povidone (Kollidon 12PF or Kollidon 17PF), poloxamer, polyethyleneglycol and polysorbate, and a mixture thereof.

The solubilizing agent to forms a hydrogen bond with acetaminophen in the injection to increase solubility, and blocks intermolecular bond of acetaminophen to prevent a generation of re-crystallization or precipitation. In addition, the solubilizing agent functions to delay a generation of recrystallization at a temperature of room temperature or less.

The solubilizing agent is mixed in the amount of 0.01 to 10 wt % in the whole injection composition. The solubilizing agent may be preferably mixed in the amount of 0.1 to 10 wt %, and more preferably mixed in the amount of 0.5 to 5 wt %. When the content of the solubilizing agent is too low, acetaminophen may not be sufficiently dissolved in the injection, and in particular, solubility of acetaminophen is lowered at a low temperature, and thus a precipitate may be educed. When the content of the solubilizing agent is too large, the solubilizing agent itself may not be sufficiently dissolved in the injection. Particularly, when the solubilizing agent is the water-soluble polymer, the solubilizing agent may increase viscosity of the injection to lead to inadequate results for use as the injection.

The toxic inhibiting material may be any one selected from N-acetylcysteine (NAC), methionine and glutathione, or a mixture thereof. The toxic inhibiting material functions to effectively decompose N-acetyl-p-benzoquinoneimine (NAPQI) which is a toxic substance produced during hepatic metabolism of acetaminophen into cysteine and aceta-mercaptate which are non-toxic metabolites, and to excrete them through a kidney.

The toxic inhibiting material is mixed in the amount of 0.05 to 5 wt % in the whole injection composition. The toxic inhibiting material may be preferably mixed in the amount of 0.1 to 5 wt %, and more preferably mixed in the amount of 0.5 to 5 wt %. When the content of the toxic inhibiting material is too low, the toxic inhibiting material may not effectively decompose NAPQI (N-acetyl-p-benzoquinoneimine) produced during hepatic metabolism of acetaminophen. In addition, when the content of the toxic inhibiting material is too high, a toxic substance caused by the toxicity inhibiting material itself may cause side effects in a human body.

The isotonic agent may be any one selected from sugar alcohols including mannitol, erythritol, glucose or trehalose, and sodium chloride (NaCl), or a mixture thereof. The isotonic agent functions to regulate osmotic pressure of the injection to prevent a patient from feeling pain at an injection site when the injection is administered to a human body.

The isotonic agent is mixed in the amount of 0.1 to 10 wt % in the whole injection composition. The isotonic agent may be preferably mixed in the amount of 0.2 to 10 wt %, and more preferably mixed in the amount of 0.5 to 5 wt %. When the content of the isotonic agent is too much or too small, osmotic pressure of the injection composition cannot be properly maintained, which may cause inconvenience such as pain or foreign body sensation when the injection is administered to a patient.

The antioxidant may be any one selected from sodium bisulfite, sodium pyrosulfite and cysteine, or a mixture thereof. The antioxidant prevents a solution property, such as a pH, from being changed by oxidation in the injection.

The antioxidant is mixed in the amount of 0.001 to 5 wt % in the whole injection composition. The antioxidant may be preferably mixed in the amount of 0.01 to 5 wt %, and more preferably mixed in the amount of 0.01 to 1 wt %. When the content of the antioxidant is too small, oxidation of the injection may not be appropriately prevented. When the content of the antioxidant is too high, the antioxidant may cause side effects such as toxic nephrosis when the injection is administered to a human body.

In addition, the injection composition may have a pH of 4 to 8. The injection composition may preferably have a pH of 4.5 to 7, and more preferably have a pH of 5 to 6.

Below, specific Examples of the present invention are described.

A. Preparation of the Injection Containing Acetaminophen.

Table 1 shows acetaminophen injection compositions. The Injections containing acetaminophen were prepared with various compositions as shown in following Table 1. In Table 1, the compositions W1 to W7 are the injection compositions according to Examples of the present invention, and the compositions W8 to W10 are the injection compositions according to Comparative examples.

First, some of sterile purified water used for the injection was put into a manufacturing container, and the solubilizing agent, the toxic inhibiting material and the isotonic agent, each of which having the predetermined content, were sequentially added to and completely dissolved in the sterile purified water to prepare an injection solution. The pH of the injection solution was measured, and an appropriate amount of a pH adjusting agent was added to the injection solution to adjust the pH to 5.5. In addition, the appropriate amount of acetaminophen was slowly added to the injection solution to be completely dissolved and to allow the injection solution to be aligned with a marked line, and the pH was then confirmed to prepare the injection. The injection was filtered with a filter having a size of 0.2 μm, an injection container was filled with the injection, and was capped with an aluminum cap after inserting a rubber stopper. In the injection preparation/filtering/filling/capping processes, air was replaced with nitrogen to minimize dissolved oxygen.

TABLE 1

| Composition | W1 | W2 | W3 | W4 | W5 | W6 | W7 | W8 | W9 | W10 |
|---|---|---|---|---|---|---|---|---|---|---|
| Acetaminophen | 2.0 | 1.0 | 1.0 | 5.0 | 1.0 | 1.0 | 5.0 | 1.0 | 1.0 | 1.0 |
| Mannitol | 1.0 | 1.0 | 2.0 | 5.0 | 2.0 | 1.0 | 1.0 | 1.0 | 12.0 | 2.0 |
| Arginine | 2.0 | 1.0 | 1.0 | — | — | — | — | 0.005 | 0.005 | — |
| Kollidon12PF | — | — | — | 1.0 | 5.0 | — | — | — | — | — |
| Kollidon17PF | — | — | — | — | — | 1.0 | 5.0 | — | — | — |
| N-acetylcysteine | 2.0 | 1.0 | 0.5 | 2.0 | 5.0 | 5.0 | 1.0 | 1.0 | 2.0 | 1.0 |
| Cysteine | 0.05 | 0.1 | 0.5 | 0.025 | 0.1 | 0.025 | 0.1 | 6.0 | 0.05 | 0.5 |
| Purified water | The rest | The rest | The rest | The rest | The rest | The rest | The rest | The rest | The rest | The rest |

B. Confirmation of Physical Properties of the Injection Containing Acetaminophen The physical properties of the injections according to the compositions of Table 1 were evaluated, and the results are shown in Table 2. Appearances were visually observed and pH was measured with a pH meter (Orion A 211, Thermo Scientific). The content of acetaminophen was analyzed by HPLC (Infinity II, Agilent) and the osmotic pressure was measured by Osmometer (OSMOMAT 3000D, Gonotec) according to each analysis condition and an operating method. Table 2 shows the result of evaluation of physical properties of the injections containing acetaminophen.

TABLE 2

| Composition | W1 | W2 | W3 | W4 | W5 | W6 | W7 | W8 | W9 | W10 |
|---|---|---|---|---|---|---|---|---|---|---|
| Appearance | Colorlessness | Colorlessness | Colorlessness | Colorlessness | Colorlessness | Colorlessness | Colorlessness | Colorlessness | Colorlessness | Colorlessness |
| pH | 5.53 | 5.35 | 5.43 | 5.51 | 5.63 | 5.35 | 5.38 | 5.35 | 5.45 | 5.50 |
| Content of acetaminophen (%) | 101.0 | 100.5 | 102.0 | 101.0 | 101.0 | 100.0 | 100.5 | 100.6 | 100.2 | 99.98 |
| Osmotic pressure (mOsmol/kg) | 300 | 290 | 289 | 291 | 290 | 295 | 289 | 280 | 280 | 270 |

As shown in Table 2, all of the injections were colorless and transparent, it was confirmed that the content of acetaminophen of each of the injection compositions was also within the criteria (95 to 105%), and it was confirmed that the pH of each of the injection compositions was between 5 and 6.

C. Test for Low-Temperature Stability

The injections according to the compositions of Table 1 were stored for 1 month under the condition of temperature of 4° C., and then left at room temperature for 1 hour, and their physical properties were checked to evaluate their low-temperature stability. Table 3 shows the result of evaluation for low-temperature stability of the injections containing acetaminophen.

TABLE 3

| Composition | W1 | W2 | W3 | W4 | W5 | W6 | W7 | W8 | W9 | W10 |
|---|---|---|---|---|---|---|---|---|---|---|
| Appearance | Colorlessness | Colorlessness | Colorlessness | Colorlessness | Colorlessness | Colorlessness | Colorlessness | Recrystallization | Recrystallization | Recrystallization |
| pH | 5.53 | 5.35 | 5.43 | 5.51 | 5.63 | 5.35 | 5.38 | 5.35 | 5.45 | 5.50 |
| Content of acetaminophen (%) | 101.0 | 100.5 | 102.0 | 101.0 | 101.0 | 100.0 | 100.5 | 89.0 | 80.3 | 80.6 |
| Osmotic pressure (mOsmol/kg) | 300 | 290 | 289 | 291 | 290 | 295 | 289 | 273 | 270 | 260 |

As shown in Table 3, it was confirmed that the compositions W1 to W7 maintained colorless transparent appearance, while it was confirmed that, in the compositions W8 to W10, acetaminophen was recrystallized and thus precipitation occurred. Therefore, it was judged that the compositions W8 to W10 had relatively low-temperature stability and were thus not suitable as the injection. The injections of the composition W8 to W10 may cause vascular embolism or the like when administered to a patient, which may be a deadly threat to a patient's life.

D. Test for Accelerated Stability

The injections according to the compositions of Table 1 were stored for 2 months under the condition of temperature of 40° C., and their physical properties were then checked to evaluate the accelerated stability. Table 4 shows the result of evaluation for the acceleration stability of the injections containing acetaminophen.

TABLE 4

| Composition | W1 | W2 | W3 | W4 | W5 | W6 | W7 | W8 | W9 | W10 |
|---|---|---|---|---|---|---|---|---|---|---|
| Appearance | Colorlessness | Colorlessness | Colorlessness | Colorlessness | Colorlessness | Colorlessness | Colorlessness | Light yellow | Light yellow | Light yellow |
| pH | 5.53 | 5.35 | 5.43 | 5.51 | 5.63 | 5.35 | 5.38 | 5.01 | 4.97 | 5.10 |
| Content of acetaminophen (%) | 101.0 | 100.5 | 102.0 | 101.0 | 101.0 | 100.0 | 100.5 | 95.0 | 94.7 | 96.3 |
| Osmotic pressure (mOsmol/kg) | 300 | 290 | 289 | 291 | 290 | 295 | 289 | 275 | 273 | 265 |

As shown in Table 4, it was confirmed that the compositions W1 to W7 were barely changed in terms of the appearance and the pH thereof, and the content and the osmotic pressure of acetaminophen, however the appearance of each of the compositions W8 to W10 was changed into yellow and the content of acetaminophen was reduced. It is judged that the above results are considered to be due to the phenomenon that acetaminophen in each of the compositions W8 to W10 was dissolved to be converted into benzoquinone.

E. Test for Stability Under Harsh Condition

The injections according to the compositions of Table 1 were stored for one month under the condition of temperature of 60° C., and the physical properties were checked to evaluate the stability under harsh condition. Table 5 shows the result of evaluation for stability of the injections containing acetaminophen, under harsh condition.

TABLE 5

| Composition | W1 | W2 | W3 | W4 | W5 | W6 | W7 | W8 | W9 | W10 |
|---|---|---|---|---|---|---|---|---|---|---|
| Appearance | Colorlessness | Colorlessness | Colorlessness | Colorlessness | Colorlessness | Colorlessness | Colorlessness | Brown | Brown | Brown |
| pH | 5.53 | 5.35 | 5.43 | 5.51 | 5.63 | 5.35 | 5.38 | 5.01 | 4.97 | 5.10 |
| Content of acetaminophen (%) | 101.0 | 100.5 | 102.0 | 101.0 | 101.0 | 100.0 | 100.5 | 87.0 | 89.6 | 87.9 |
| Osmotic Pressure (mOsmol/kg) | 300 | 290 | 289 | 291 | 290 | 295 | 289 | 260 | 259 | 261 |

As shown in Table 5, it was confirmed that the compositions W1 to W7 showed almost no change in properties, pH, acetaminophen content and osmotic pressure, but an appearance of each of the compositions W8 to W10 was changed to brown and the content of acetaminophen was decreased. It is judged that the compositions W8 to W10 were decomposed faster than that in the accelerated test and the appearance thereof was changed into a brown color.

F. Hepatotoxicity Test

Experiments for the hepatotoxicity test were conducted after dividing specific pathogen free (SPF) mice (C57BL/6NCrljOri mice), which have been typically employed, into ten mice for each group. The experiments were conducted after being received in advance approval by the Institutional Animal Care and Use Committee (Approval number: 17M034) according to the "Animal Protection Law" (Law No. 4379 legislated on May 31, 1991 and partially revised on Jan. 20, 2015. The experimental animals were used for the test after being acclimated for one week. It was decided to administer the injection of 300 mg/kg, which is hepatotoxicity-inducing dose confirmed by a preliminary test, to an abdominal cavity. The injection was administered once, general symptoms were observed for 24 hours, and blood was sampled from aorta *abdominalis* after 24 hours. Sampled blood was contained in a tube in which no anti-coagulant exists, and was left for at least 90 minutes under the condition of room temperature. Then, blood was is centrifuged (300 rpm, 10 minute and 4° C.) to separate serum, and blood biochemical examination was conducted using the blood biochemical analyzer (HITACH 7180, HITACHI, JAPAN).

Aspartate aminotransferase (AST), alanine aminotransferase (ALT), alkaline phosphatase (ALP), total bile acid (TBA), total bilirubin (T-BIL) were measured. Table 6 shows the results of evaluation of changes in the liver index of the acetaminophen injection composition.

TABLE 6

| Classification | Saline | W0 | W1 | W2 | W3 | W4 | W5 | W6 | W7 |
|---|---|---|---|---|---|---|---|---|---|
| AST | 41.8 | 6488.3 | 46.2 | 45.5 | 1299.1 | 45.3 | 46.3 | 47.6 | 48.5 |
| ALT | 22.7 | 11129.1 | 33.0 | 50.6 | 3239.7 | 35.0 | 45.4 | 36.7 | 40.7 |
| ALP | 284.4 | 417.7 | 250.6 | 275.3 | 282.3 | 248.5 | 267.4 | 276.1 | 2802 |
| TBA | 13.5 | 114.0 | 22.5 | 4.9 | 44.5 | 15.3 | 16.3 | 23.4 | 19.3 |
| T-BIL | 0.032 | 0.082 | 0.055 | 0.051 | 0.091 | 0.042 | 0.056 | 0.054 | 0.062 |

*W0: Existing product, Profa Infusion Inj. (Lot No: 48R9FE0, Dai Han Pharm. Co., Ltd, in Republic of Korea)

As shown in Table 6, As a result of administering 300 mg/kg, which is the concentration by which hepatotoxicity is induced, it was confirmed that, in W0 which the positive control group, hepatotoxicity was observed in the indexes of AST, ALT, ALP, TBA, T-BIL. Table 6 shows that, regarding the compositions W1 to W7 of Table 1, each hepatotoxicity index is similar to saline (0.9% NaCl solution for intravenous injection) which is the negative control group. This shows that even though acetaminophen having the concentration by which hepatotoxicity is induced is administered, it is possible to prevent hepatotoxicity from occurring in the composition containing the toxic inhibiting material.

The invention claimed is:

1. An injection composition containing acetaminophen, comprising:
   acetaminophen mixed in the amount of 0.01 to 5 wt %;
   a solubilizing agent mixed in the amount of 1.0 to 2.0 wt %;
   a toxic inhibiting material mixed in the amount of 0.05 to 2.0 wt %;
   an isotonic agent mixed in the amount of 0.1 to 10 wt %;
   an antioxidant mixed in the amount of 0.025 to 0.05 wt %; and
   the rest of sterile purified water for injection,
   wherein the antioxidant is cysteine,
   wherein the toxic inhibiting material is N-acetylcysteine,
   wherein the solubilizing agent is arginine.

2. The injection composition containing acetaminophen of claim 1, wherein the injection composition has a pH of 4 to 8.

3. The injection composition containing acetaminophen of claim 1, wherein the isotonic agent is any sugar alcohol selected from the group consisting of mannitol, erythritol, glucose and trehalose, and sodium chloride (NaCl), or a mixture thereof.

4. An injection composition containing acetaminophen, comprising:
   acetaminophen mixed in the amount of 0.5 to 2 wt %;
   a solubilizing agent mixed in the amount of 1.0 to 2.0 wt %;
   a toxic inhibiting material mixed in the amount of 0.05 to 2.0 wt %;
   an isotonic agent mixed in the amount of 0.5 to 5 wt %;
   an antioxidant mixed in the amount of 0.025 to 0.05 wt %; and
   the rest of sterile purified water for injection,
   wherein the antioxidant is cysteine,
   wherein the toxic inhibiting material is N-acetylcysteine,
   wherein the solubilizing agent is arginine.

5. The injection composition containing acetaminophen of claim 4, wherein the injection composition has a pH of 5 to 6.

6. The injection composition containing acetaminophen of claim 4, wherein the isotonic agent is any sugar alcohol selected from the group consisting of mannitol, erythritol, glucose and trehalose, and sodium chloride (NaCl), or a mixture thereof.

* * * * *